US012324887B2

(12) United States Patent
Ingalls et al.

(10) Patent No.: US 12,324,887 B2
(45) Date of Patent: *Jun. 10, 2025

(54) MICROMINIATURE PATTERNED METAL ON MEDICAL GRADE BALLOONS

(71) Applicant: Professional Plating Inc., Anoka, MN (US)

(72) Inventors: Craig A. Ingalls, Burnsville, MN (US); David R. Kaar, Minneapolis, MN (US); Ross William Peterson, Ramsey, MN (US)

(73) Assignee: Professional Plating Inc., Anoka, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/132,855

(22) Filed: Apr. 10, 2023

(65) Prior Publication Data
US 2023/0241362 A1  Aug. 3, 2023

Related U.S. Application Data

(63) Continuation of application No. 16/540,225, filed on Aug. 14, 2019, now Pat. No. 11,690,982.
(Continued)

(51) Int. Cl.
*C23C 14/14* (2006.01)
*A61B 5/00* (2006.01)
(Continued)

(52) U.S. Cl.
CPC ........... *A61M 25/1029* (2013.01); *A61B 5/25* (2021.01); *A61B 5/6853* (2013.01);
(Continued)

(58) Field of Classification Search
CPC ...... A61B 18/1492; A61B 2018/00577; A61B 2018/00214; A61B 2018/0022;
(Continued)

(56) References Cited

U.S. PATENT DOCUMENTS 4,952,357 A  8/1990 Euteneuer
5,207,700 A  5/1993 Euteneuer
(Continued)

FOREIGN PATENT DOCUMENTS

WO  2019/038636 A1  2/2019

*Primary Examiner* — Joseph A Stoklosa
*Assistant Examiner* — Brian M Antiskay
(74) *Attorney, Agent, or Firm* — Shewchuk IP Services, LLC; Jeffrey D. Shewchuk

(57) ABSTRACT

A thin walled balloon formed in polymer tubing has a patterned metal layer on its outer surface, created by physical vapor deposition (PVD). The pattern is defined by a stencil mask assembled around the balloon, with the balloon inflated therein. The PVD occurs without deforming or degrading the polymer material of the balloon, by actively pulling heat away from the balloon a) by forming the stencil mask out of metal; b) by providing a metal heat conduction path away from the balloon to a heat sink, such as outside the vacuum chamber, and/or c) by flow of a cooling fluid within the balloon during the PVD process. Proper PVD process parameters are selected to minimize heat generation, such as having argon pressure in the range of 0.8 to 1.2 milli-torr and generating the plasma at a power of less than about 200 watts/square inch of effective target surface area.

17 Claims, 9 Drawing Sheets

Related U.S. Application Data

(60) Provisional application No. 62/719,042, filed on Aug. 16, 2018.

(51) Int. Cl.

| | |
|---|---|
| *A61B 5/25* | (2021.01) |
| *A61B 18/18* | (2006.01) |
| *A61M 25/10* | (2013.01) |
| *C23C 14/04* | (2006.01) |
| *C23C 14/20* | (2006.01) |
| *C23C 14/34* | (2006.01) |
| *C23C 14/54* | (2006.01) |
| *C23C 14/56* | (2006.01) |

(52) U.S. Cl.
CPC ............ *C23C 14/042* (2013.01); *C23C 14/20* (2013.01); *C23C 14/34* (2013.01); *C23C 14/54* (2013.01); *C23C 14/56* (2013.01); *A61M 2025/1031* (2013.01); *A61M 2025/1075* (2013.01)

(58) Field of Classification Search
CPC .......... A61B 2018/00267; A61B 5/287; A61B 2018/00351; A61B 2017/00243; A61B 5/6852; A61B 2018/1497; A61B 5/6869; A61B 1/00082; A61N 1/057; A61N 1/362; A61N 1/04; A61M 25/10; A61M 25/1002; A61M 2210/125
USPC ................ 600/372–375, 377, 381, 393, 435, 600/508–509; 604/95.03–95.04, 96.01, 604/97.01, 102.01, 103.06, 103.07, 604/103.11; 606/20–42
See application file for complete search history.

(56) References Cited

U.S. PATENT DOCUMENTS

| | | |
|---|---|---|
| 5,352,199 A | 10/1994 | Tower |
| 5,499,980 A | 3/1996 | Euteneuer |
| 5,609,606 A | 3/1997 | O'Boyle |
| 5,611,807 A | 3/1997 | O'Boyle |
| 5,718,684 A | 2/1998 | Gupta |
| 5,782,742 A | 7/1998 | Crocker et al. |
| 5,865,801 A | 2/1999 | Houser |
| 6,176,821 B1 | 1/2001 | Crocker et al. |
| 6,500,108 B1 | 12/2002 | Sorensen et al. |
| 6,572,813 B1 | 6/2003 | Zhang et al. |
| 6,699,170 B1 | 3/2004 | Crocker et al. |
| 6,761,708 B1 | 7/2004 | Chiu et al. |
| 7,189,229 B2 | 3/2007 | Lopath et al. |
| 7,264,458 B2 | 9/2007 | Holman et al. |
| 7,708,928 B2 | 5/2010 | Holman et al. |
| 9,622,680 B2 | 4/2017 | Ghaffari et al. |
| 9,662,069 B2 | 5/2017 | De Graff et al. |
| 10,524,859 B2 | 1/2020 | Vrba et al. |
| 2002/0177765 A1* | 11/2002 | Bowe ................ A61B 18/1492 600/374 |
| 2003/0195510 A1* | 10/2003 | Schaer .............. A61B 18/1492 606/41 |
| 2004/0054367 A1 | 3/2004 | Jimenez, Jr. et al. |
| 2012/0064141 A1 | 3/2012 | Andreacchi et al. |
| 2013/0090599 A1 | 4/2013 | Mchugh |
| 2013/0330498 A1 | 12/2013 | Hogg et al. |
| 2015/0141917 A1* | 5/2015 | Tilson .................. A61F 2/2433 604/103.09 |
| 2015/0141982 A1* | 5/2015 | Lee ....................... A61B 5/287 606/41 |
| 2015/0320472 A1* | 11/2015 | Ghaffari ................ A61B 18/24 606/21 |
| 2017/0042615 A1* | 2/2017 | Salahieh ................. A61B 5/01 |
| 2017/0287770 A1 | 10/2017 | Gangakhedkar et al. |
| 2017/0312022 A1* | 11/2017 | Beeckler .............. A61B 5/6857 |
| 2018/0229011 A1 | 8/2018 | Govari et al. |
| 2019/0060622 A1 | 2/2019 | Beeckler |
| 2019/0175262 A1 | 6/2019 | Govari et al. |

* cited by examiner

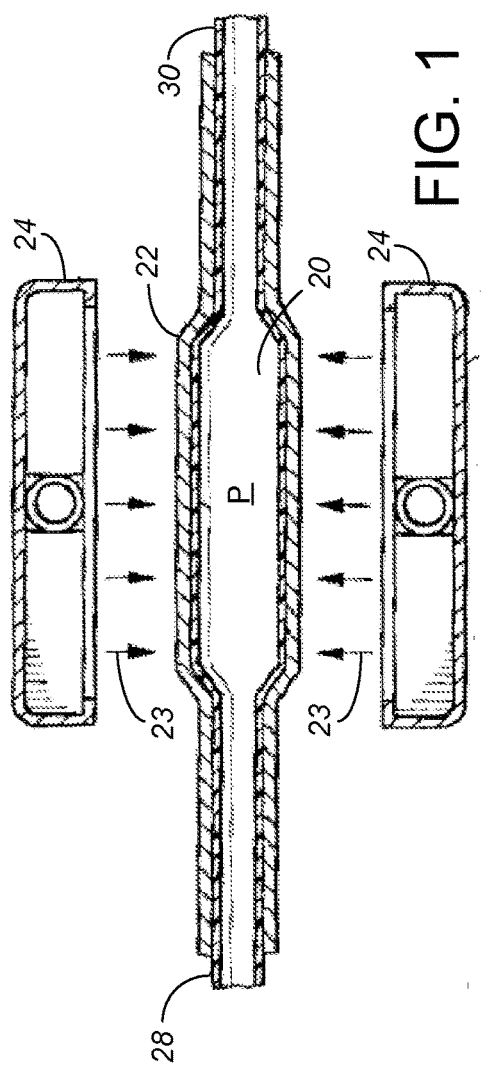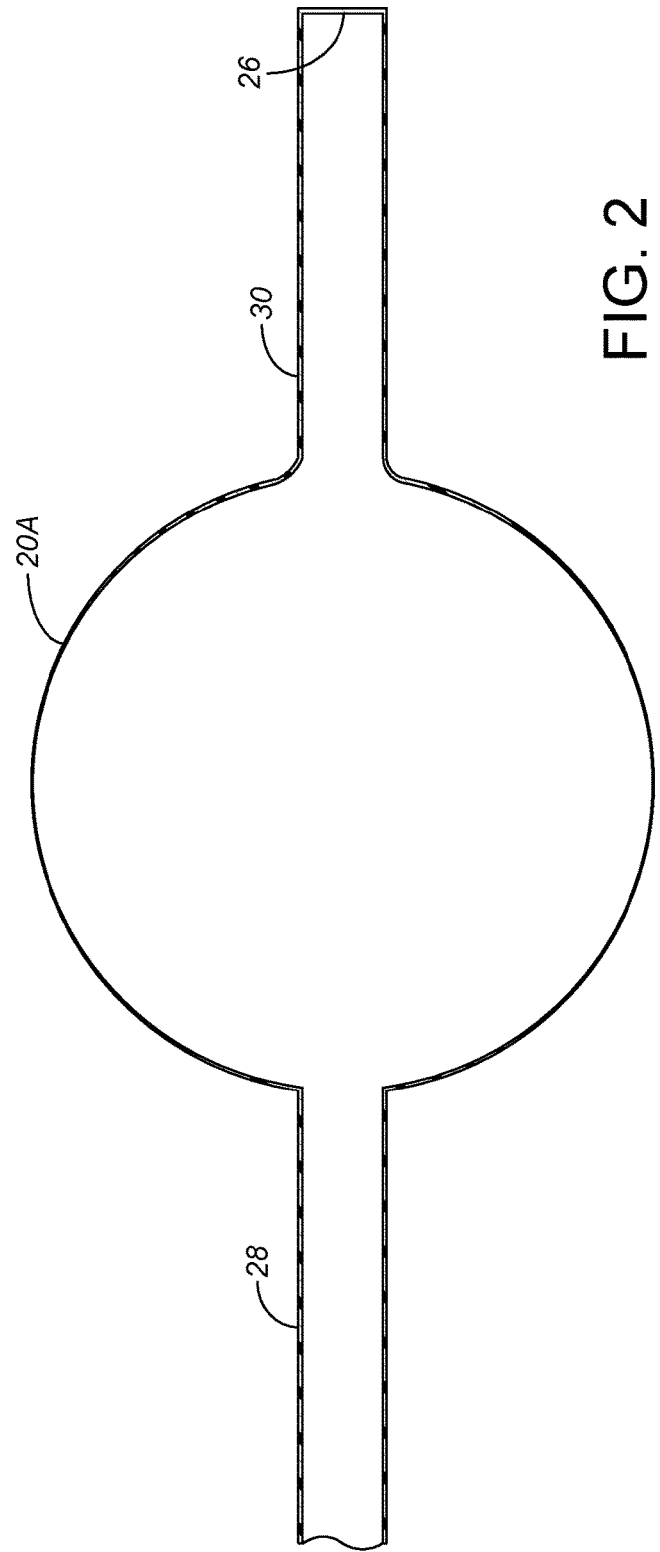

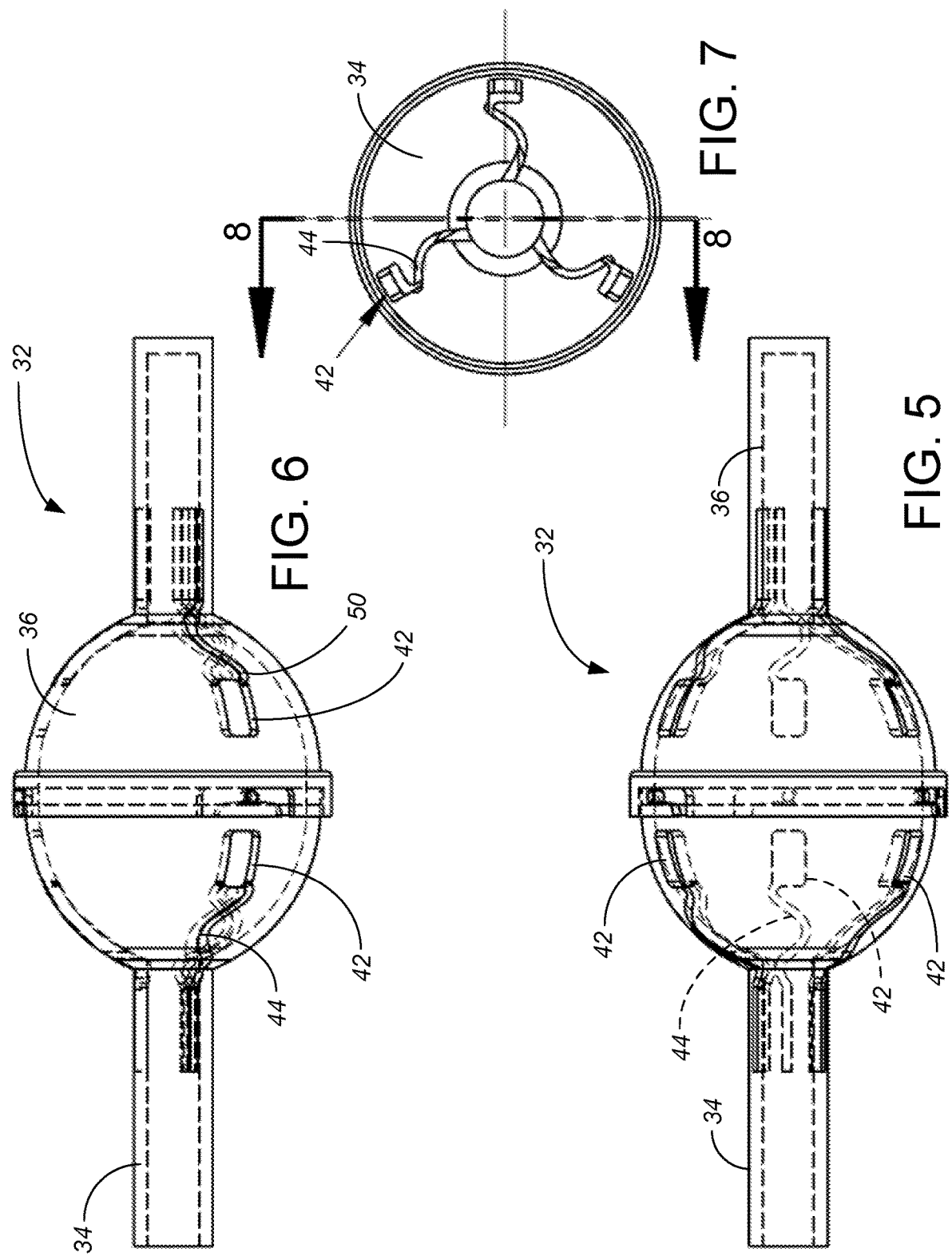

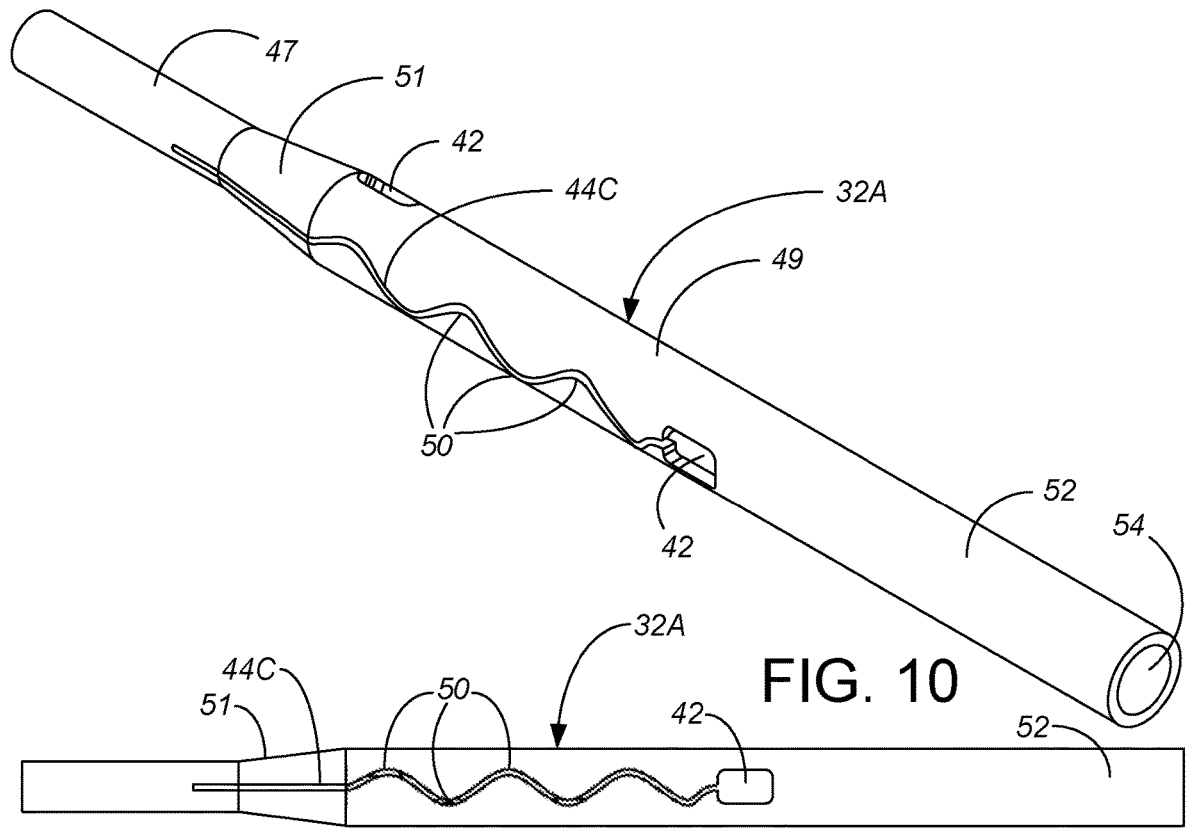
FIG. 10
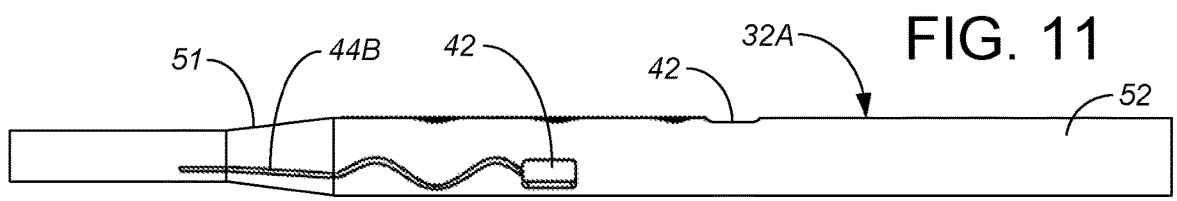
FIG. 11
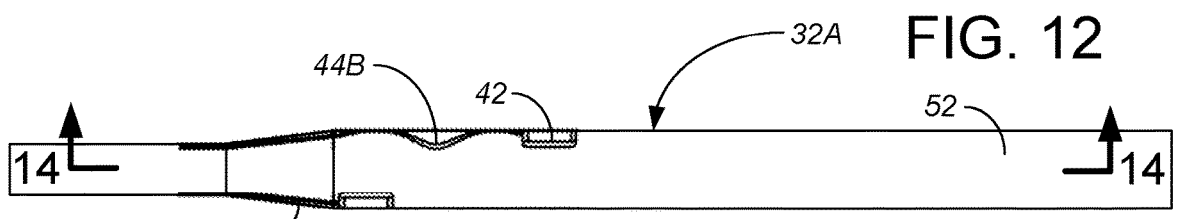
FIG. 12
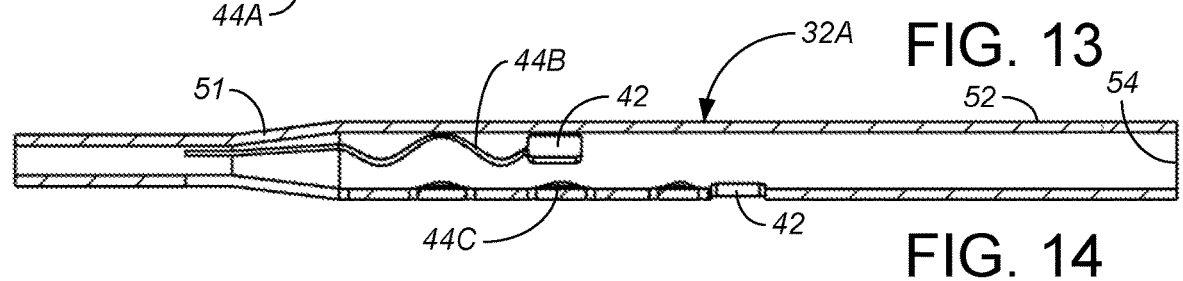
FIG. 13
FIG. 14

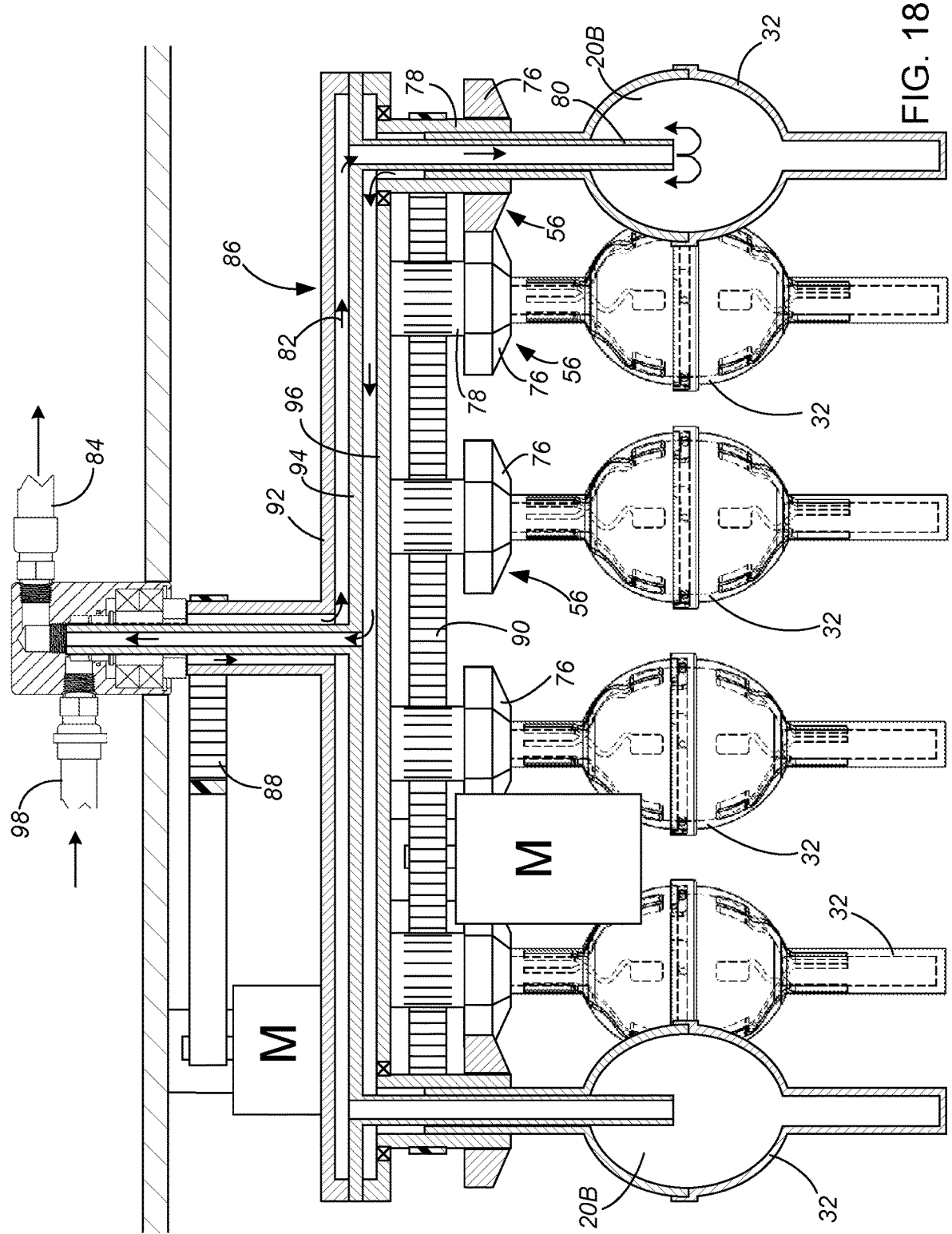

MICROMINIATURE PATTERNED METAL ON MEDICAL GRADE BALLOONS

CROSS-REFERENCE TO RELATED APPLICATION(S)

The present application is a continuing application from U.S. application Ser. No. 16/540,225 entitled MICROMINIATURE PATTERNED METAL ON MEDICAL GRADE BALLOONS, filed Aug. 14, 2019, and claims priority from U.S. Provisional Application No. 62/719,042 entitled PATTERNED METAL ON MICROMINIATURE BALLOONS, filed Aug. 16, 2018, both incorporated herein by reference.

BACKGROUND OF THE INVENTION

The present invention is directed to applying metal layers on polymers, particularly for use in the field of microminiature devices such as used in internal health care for deployment by a catheter.

In catheter devices, balloons have been used, positioned within the human body in a deflated state, and the enlarged in situ by introducing a pressurized fluid within the balloon. Some such balloon catheters include a metal layer, and placing a metal layer on a balloon catheter is one such medical industry application for which standard electroless plating is unacceptable. For instance, U.S. Pat. Nos. 9,622,680, 6,761,708, 6,699,170, 6,500,108, 6,176,821, 5,782,742, 5,611,807, 5,609,606, 5,499,980, 5,207,700 and 4,952,357 all disclose balloon catheters that can make use of metal layers. Each of these patents are incorporated by reference.

Metal on polymers was first widely used by the automotive industry in the 1960s, and is commonly achieved through an electroless plating process. Traditionally, before a metal coating can be applied, a chemical etching process is performed to prepare the surface of the polymer substrate. The chemical etching process traditionally used to prepare the plastic surface for plating involves toxic chromic acid-based solutions. Although this may be beneficial for adhesion and an acceptable process for the automotive industry, this toxic surface preparation is not acceptable for medical industry applications such as catheter balloons.

There are alternatives to electroless plating to provide a metal layer on a polymer, such as adhesive backed metallic foil, such as gold foil with adhesive backing. For many medical industry applications, the adhesive backing does not have sufficient bonding strength. For a different subset of medical industry applications, the adhesive backed metallic foil adds too much thickness to the polymer substrate.

Another alternative is to paint the polymer substrate with a metallic filled paint so that the layer of paint is conductive and electroplating can then be applied. However this method is also problematic in critical applications like medical devices due to the bond being only as strong as the paint, which causes adhesion failures. Also, though perhaps thinner than most adhesive backed metallic foils, resin coatings such as paint are still limited as to how thin they can be applied. A typical resin, such as an acrylic or epoxy, will form a layer whose dry thickness is one the order of 0.003" (about 75 microns). The thickness of the resin coatings can create design challenges where space constraints are significant. The metallic filled pain layers often cannot be folded, flexed, or stretched (expanded and/or contracted) with the same or similar plastic or elastic properties that the base polymer substrate has, particularly when the base polymer substrate itself is quite thin such as on a catheter balloon.

Nano-particle conductive inks can be CNC printed on polymer substrates, but have similar issues in terms of poor adhesion properties to the base substrate and thickness. Another major drawback of nano-particle conductive inks (such as a silver nano-particle ink) is that in order to achieve electrical conductivity and adhesion the ink must be sintered, which will often thermally degrade the polymer base substrate due to the high sintering temperatures.

A different approach to these methods involves Physical Vapor Deposition ("PVD"), also sometimes called Chemical Vapor Deposition, or sputtering. PVD has sometimes been used to deposit metallic films on thin walled polymer structures used in medical devices and procedures, and several of the above-referenced balloon catheter patents refer to PVD or sputtering. Sputtering is a well-developed technology for depositing thin coatings of one material (the deposited layer, or deposition layer) on another material (the substrate). The deposition layer is typically a metal but can also be a semiconductor and less often an oxide, nitride, or carbon compound. The PVD deposition process starts in a vacuum chamber under high vacuum (typically on the order of 0.1 millitorr) to prevent unwanted oxidation or other reactions and to allow the transit of the deposition material from the sputter target to the substrate. The vacuum chamber is then backfilled with an inert carrier or process gas, most typically argon. Neon and krypton may also be used, but helium is considered unsuitable because its low mass makes it inefficient in the deposition process. Nitrogen and oxygen can also be used for the process gas for some materials. The sputtering process requires the production of a plasma by a plasma power source which electrically induces ionization of the inert carrier gas from the residual inert gas in the vacuum chamber. The (argon) ions in the plasma, accelerated by the applied high plasma voltage, bombard the target material in turn freeing donor atoms of the target which migrate in the vacuum to the substrate, forming the deposition layer. The sputtering gun (also called a magnetron gun) surrounds the target and forms a magnetic tunnel to direct the metal atoms toward the substrate for deposition. Typical sputtering (i.e. metal films or metals, semiconductors or ceramics) use high power (1 kW) to the target, high voltage (100V-1600V and more) to ionize the gas, and high current (0.5-1.5 amps), to produce a high flux of gas ions onto the target and a high flux of target atoms to the substrate.

However, the PVD process usually heats up the substrate to relatively high temperatures (several hundred degrees centigrade). Standard PVD methods can accordingly cause melting, thermal deformation or degradation to the polymeric substrate material of the catheter balloon, limiting or destroying the utility of the final construct. The above-referenced patents each provide little or no description of the particular method of manufacturing used to fabricate the metal layer on the balloon, particularly in a way that allows the metal layer to occupy a distinct shape less than a complete covering of the balloon, and without causing thermal deformation or degradation to the balloon.

Other alternatives for electrodes and leads on in-vivo devices like catheter balloons and shafts include wires, machined components, imbedding/compounding, etc. Metal leads may be soldered or glued to pads. Wire leads may be embedded on polymer substrate. Spray-on or hand applied conductive coatings may be used. These alternatives have known risks and performance disadvantages such as detachment, fracturing, loss of flexibility/malleability/foldability and increased dimensional profiles. They also can be laborious and not productive processes, and can result in less precise component tolerances. Most of these alternatives require electrical leads to the electrodes for energy transfer, which can cause device failures, increase device dimension profile, require added processing and materials resulting in higher manufacturing costs and performance disadvantages. Better solutions are needed.

BRIEF SUMMARY OF THE INVENTION

The present invention is a thin walled balloon formed in polymer tubing and having one or more PVD-deposited metallic patterns or patches on the outer surface of the balloon, preferably with an undulating lead from the patch to an end portion of the tubing, as well as a method for forming such a balloon. By using a system design which actively pulls heat away from the balloon during the PVD process and by using proper process parameters, the patterned metal layer is deposited on the balloon through a stencil mask without deforming or degrading the polymer material of the balloon.

BRIEF DESCRIPTION OF THE DRAWINGS

FIG. 1 is a simplified side cross-sectional view showing the formation of a balloon in tubing for medical use. The wall thickness shown in FIG. 1 is not to scale.

FIG. 2 is a side cross-sectional view showing an alternative balloon geometry for use in the present invention, better showing the wall thickness of the tube and the balloon to scale.

FIG. 5 is a side view of the stencil mask of FIGS. 3 and 4.

FIG. 6 is a top plan view of the stencil mask of FIGS. 3-5.

FIG. 7 is an interior end view of the proximal portion of the stencil mask of FIGS. 3-6.

FIG. 10 is a perspective view of an alternative stencil mask for use in making a microminiature metal pattern on a catheter balloon, similar in shape to the balloon of FIG. 1.

FIG. 11 is a first side view of the stencil mask of FIG. 10.

FIG. 12 is a bottom view of the stencil mask of FIGS. 10 and 11, taken 120° from FIG. 11.

FIG. 13 is a second side view of the stencil mask of FIGS. 10-12, (taken with the stencil mask rotated 180° about its longitudinal axis from FIG. 11).

FIG. 14 is a cross-sectional view of the stencil mask of FIGS. 10-13, taken along cut lines 14-14 in FIG. 13.

FIG. 18 is a schematic cross-sectional view of a second alternative PVD vacuum chamber, which uses a carousel to simultaneously deposit a metal pattern on twelve balloons using twelve of the stencil masks of FIGS. 3-9.

Figure 3:
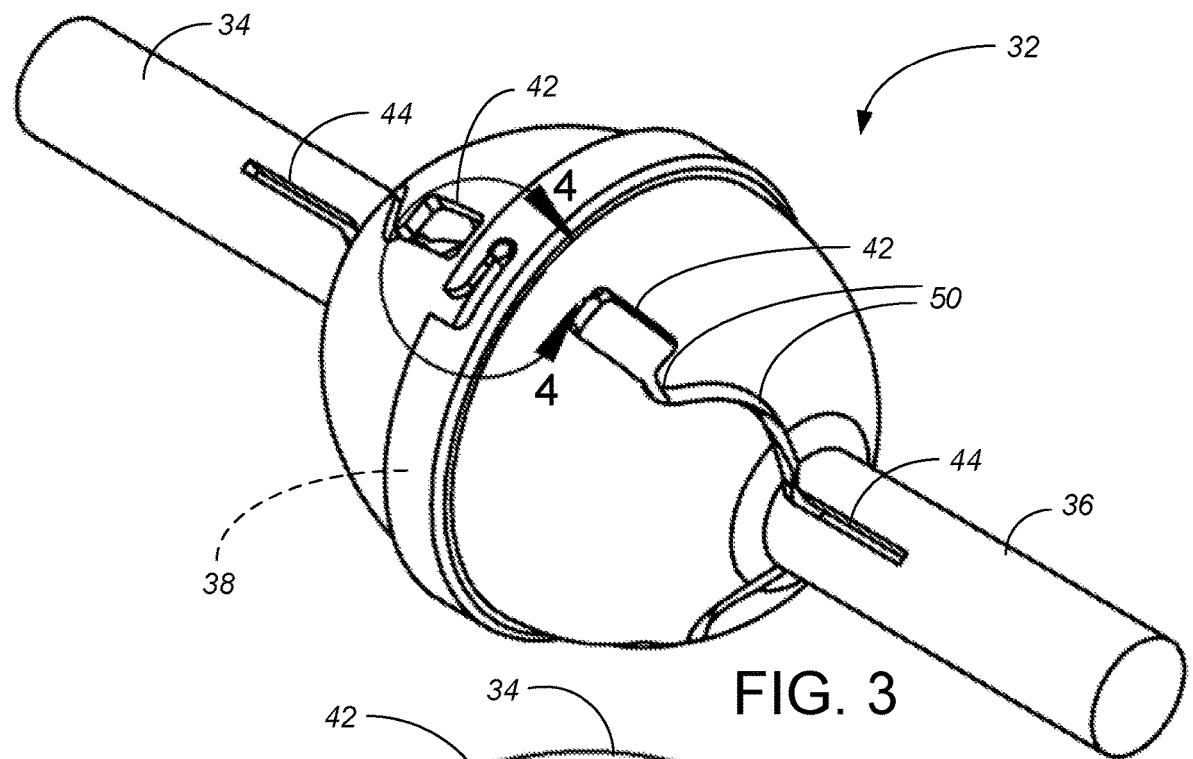
FIG. 3 is a perspective view of a preferred stencil mask as assembled for use in making a microminiature metal pattern on a catheter balloon, similar in shape to the balloon of FIG. 2 but slightly lengthened.

While the above-identified drawing figures set forth preferred embodiments, other embodiments of the present invention are also contemplated, some of which are noted in the discussion. Discussion about a general embodiment (without using the suffix "A" or "B" in the reference numeral) is often applicable to any embodiment. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION OF THE PREFERRED EMBODIMENTS

The balloons of the present invention starts as thin walled tubing which can be extruded from any of a variety of polymeric materials including but not limited to polyethylene terephthalate or "PET", urethane, polyurethane, polyimide, polyamide, Pebax, silicon and nylon (such as biaxially oriented nylon 12). Other potential materials for use in the tubing include polyethylene, polyvinyl chloride, polyarylenesulfides, mixtures of ethylene-butylene-styrene block copolymer and low molecular weight polystyrene having polypropylene optionally added thereto, and similar compositions wherein butadiene or isoprene is used instead of the ethylene and the butylene; polyester copolymers; thermoplastic rubbers; silicone-polycarbonate copolymers; ethylene-vinyl acetate copolymers; and crosslinked ethylene-vinyl acetate copolymers. The most preferred materials are PET and urethane. The tubing has dimensions suitable for catheter deployment, i.e., an outer diameter less than about 10 mm and a wall thickness less than about 2 mm. For instance, in the embodiment depicted in FIG. 1, the tubing initially has an inner diameter of about 3.3 mm and an outer diameter of about 3.6 mm, for a wall thickness of about ⅙ mm.

As shown in FIG. 1, the balloon 20 is created by placing a portion of the tubing into a mold 22 of the balloon shape and then applying heat 23 such as using heating members 24. When the tube material is sufficiently warm relative to the flow temperature of the material, internal pressure P is provided so that the tube expands against the mold walls. One easy way to provide the internal pressure from a single source is to close off the distal end of the tube such as by melting the extruded tubing closed such as with a simple thermal heat bar or impulse seal ("cauterizing" the tubing) beyond the desired location for the balloon 20, and some embodiments of the present invention make use of a closed distal end 26 as shown in FIG. 2. Further, the balloon 20 is primarily contemplated as a component for use in a balloon catheter (not shown in these figures, but shown in incorporated by reference documents), where the balloon catheter will have a distal tip designed for navigating through the human anatomy (primarily through the vascular structure), such as over a guide wire. For joining the balloon 20 over the remaining catheter structure and for inflating the balloon 20, the proximal side 28 of the tubing must extend before the start of the balloon 20, and the distal side 30 of the tubing must extend after the end of the balloon 20, such as having a minimum of 2 mm of tubing on each end of the balloon 20. As will be explained, preferred embodiments have a proximal tubing 28 and a distal tubing 30 which each extend significantly further than 2 mm, which can later be cut to a shorter length before final assembly into the catheter. For instance, the embodiment shown in FIG. 2 has a distal tubing length of about 25 mm and a proximal tubing length of about 25 mm, while the embodiment shown in FIGS. 3-9 encompasses a distal tubing length of about 23 mm and a proximal tubing length of about 30 mm. Exemplary methods for forming the balloon 20 are further detailed in U.S. Pat. Nos. 6,572,813, 7,264,458 and 7,708,928, incorporated by reference.

The balloon 20 will typically have an outer diameter which is at least 1.5 times the diameter of the proximal and distal tubing, 28, 30, up to about 50 mm in diameter. The specific shape of the balloon 20 depends upon its intended specific medical purpose, with FIG. 1 showing an example 20 of a simple cylindrical shape and FIG. 2 showing an example 20A of simple spherical shape. For instance, the cylindrical balloon 20 of FIG. 1 has an outer diameter of about 5.2 mm, and the spherical balloon 20A of FIG. 2 has an outer diameter of about 25 mm. Another preferred embodiment produces an ovoid balloon 20B (called out only in FIG. 18) used with the stencil mask 32 shown in FIGS. 3-9, having a length of about 30 mm and a diameter of about 24 mm. Other common balloon sizes have a length in the range of 6 to 30 mm and have an unexpanded diameter in the range of 1.5 to 25 mm. After the material has thermoset in the mold 22, the balloon 20 is cooled while maintaining the internal pressure P to result in the desired balloon shape. While FIGS. 1-3 depict three simple shapes, many other simple and complex shapes are known and can be used for the balloon 20, including the balloon shapes disclosed in U.S. Pat. Nos. 5,352,199, 5,718,684, 5,865,801, 6,761,708, and 7,189,229, all incorporated by reference for their teachings of balloon shapes and attachment and use of the balloon 20 in catheter deployment systems.

Note that, largely due to how the balloon 20 is formed, the balloon 20 will have a thinner wall thickness and be more flexible than the wall thickness of the tubing. For instance, FIG. 2 shows a balloon design with an outer diameter at its equator which is about seven times the diameter of the proximal and distal tubing portions 28, 30, resulting in a wall thickness at the equator of the balloon 20 of about one seventh of the wall thickness of the proximal and distal tubing portions 28, 30, such as having a balloon wall thickness in the range of 0.02-0.04 mm.

The wall thickness of the polymer at the location of the tubing 28, 30 is flexible, allowing the tubing 28, 30 and the balloon 20 to be catheter-fed through human body anatomy to a deployment location. The wall thickness of polymer at the location of the balloon 20 is not only quite flexible (referred to as a "compliant" balloon if sufficiently flexible that the balloon won't hold its own weight), but also stretchable. Thus, when a pressure differential is created with a higher pressure inside the balloon 20 than outside the balloon 20, the balloon 20 will expand (inflate) due to such pressure, and will expand significantly more than the tubing 28, 30 under the same pressure differential. It is the flexibility and stretchability of the balloon 20 that creates the medical procedure possibilities, by advancing the deflated balloon 20 to the catheter treatment site internal to the body, and then being able to inflate the balloon 20 in situ. For instance, under a 10 atm pressure difference, the balloon 20 will expand to at least 102% of its unpressurized diameter, such as within the range of 102-150% of its unpressurized diameter, and more preferably to within the range of 105-120% of its unpressurized diameter, and most preferably to within the range of 110-115% of its unpressurized diameter. For common surgical applications, the balloon 20 should have a burst pressure differential of at least 1 atm (i.e., will not burst when the pressure inside the balloon 20 is 2 atm and the pressure outside the balloon 20 is 1 atm), and more preferably a burst pressure differential of at least 10 atm, and more preferably a burst pressure differential of over 25 atm. Compliant balloons may be deflated and compressed within a sheath size significantly smaller than the balloon outer diameter, at least down to the sheath size of the original tubing 28, 30, such as down to 2-4 French.

While the creation of the balloon 20 can be viewed in some instances as an initial part of the present invention, it is also recognized that the balloon 20 may be created by a third party. As represented in FIG. 1, the proximal and distal tubing lengths can be much longer during the balloon formation process, with a cutting and/or sealing (cauterizing the distal end 26) step applied later.

The present invention utilizes PVD deposition while the balloon 20 is within a stencil mask 32 to deposit metal spots, patches or other patterns on the outside of the balloon 20, while not degrading the polymer material of the balloon 20 during the PVD deposition process. It is important that the substrate material of the balloon 20, despite its thin wall thickness, be kept thermally stable as substantial heat energy is created during the PVD deposition process. As a general statement, the present invention involves non-standard PVD process design considerations to minimize or eliminate thermal degradation of the balloon 20. The present invention also involves balloons 20 that include PVD metal patterns formed while minimizing or eliminating thermal degradation. Thermal robustness and stability of the balloon substrate is a crucial aspect for the successful application of the metal patterns.

Figure 15:
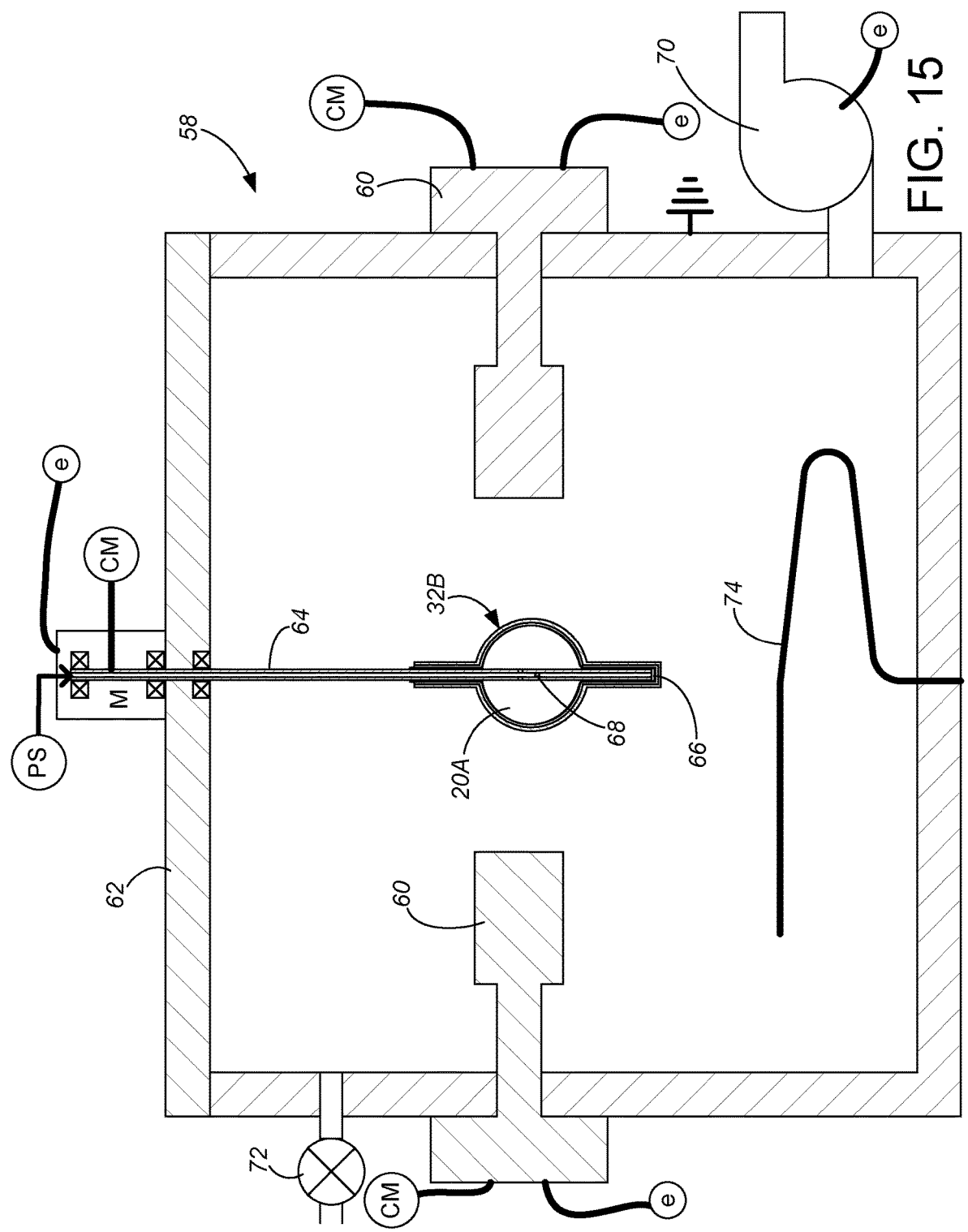
FIG. 15 is a schematic cross-sectional view of a PVD vacuum chamber, showing the depositing of a metal pattern on the balloon of FIG. 2.
Figure 16:
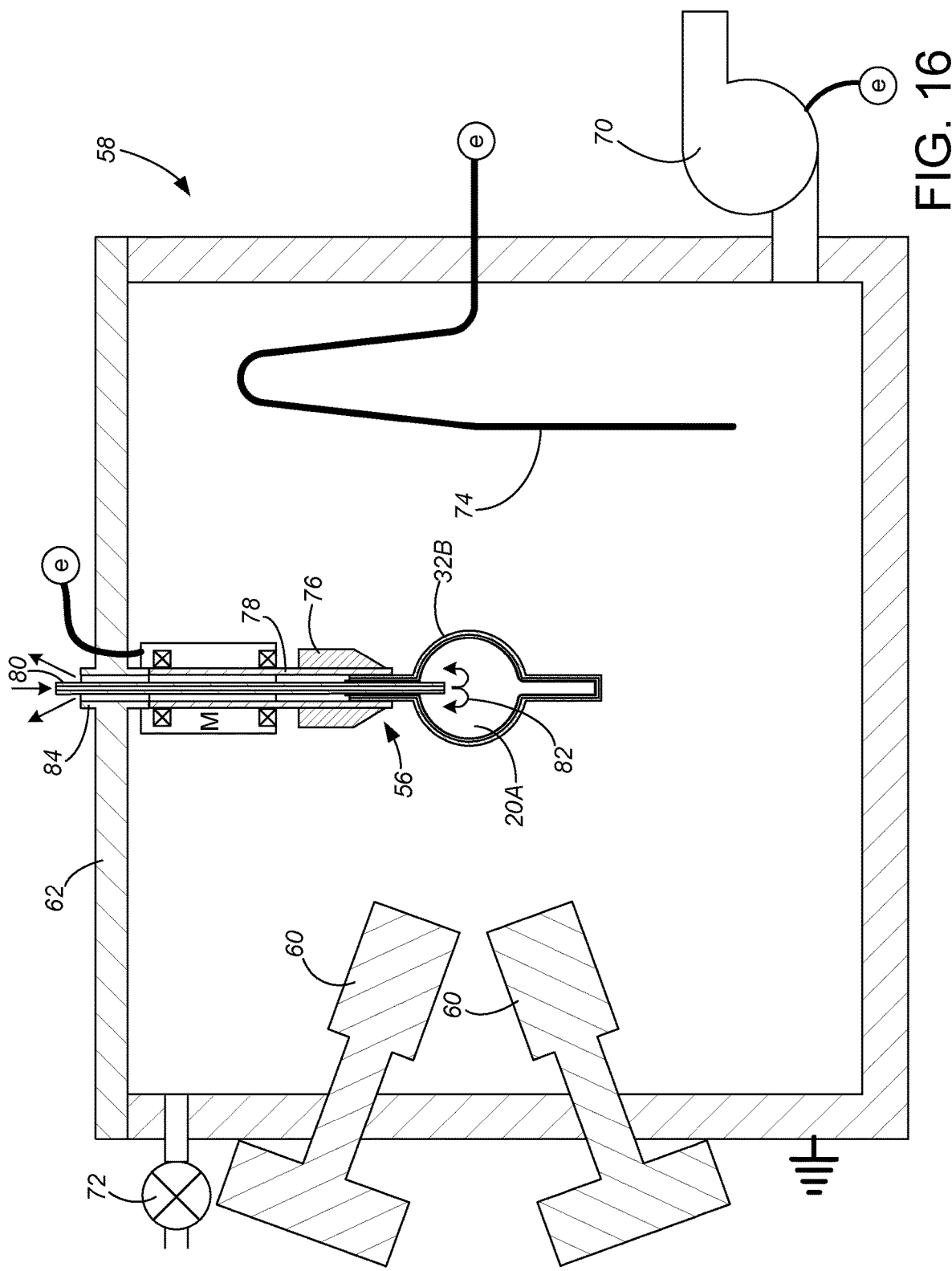
FIG. 16 is a schematic cross-sectional view of an alternative PVD vacuum chamber, showing the depositing of a metal pattern on the balloon of FIG. 2.

The stencil mask 32 is a rigid structure defining a hollow cavity for the balloon 20, with the hollow cavity being sized and shaped to match the uninflated shape of the balloon 20 with only a slight clearance (typically, a clearance on the order of 0.1 mm). FIGS. 3-9 show details of one preferred stencil mask 32 in its assembled configuration, and FIGS. 10-14 show details of a different preferred stencil mask 32A for the balloon 20 of FIG. 1. FIGS. 15 and 16 show vacuum chamber layouts using yet another different preferred stencil mask 32B for the balloon 20A of FIG. 2. The balloon 20, 20A, 20B is within the stencil mask 32, 32A, 32B during the PVD process.

With reference to the stencil mask 32 of FIGS. 3-9, the stencil mask 32 is preferably formed with two or more mask portions 34, 36 which can be assembled together around the balloon 20, contacting each other at a parting location 38. The parting location 38 is preferably at or near the equator of the balloon 20. In this embodiment, the stencil mask 32 is formed by two similarly shaped (largely hemispherical, because the balloon 20B is largely spherical) mask portions 34, 36, such that one mask portion 36 can be positioned over the distal end 30 of the tubing and one 34 positioned over the proximal end 28 of the tubing before being brought together and joined at the parting location 38.

Figure 4:
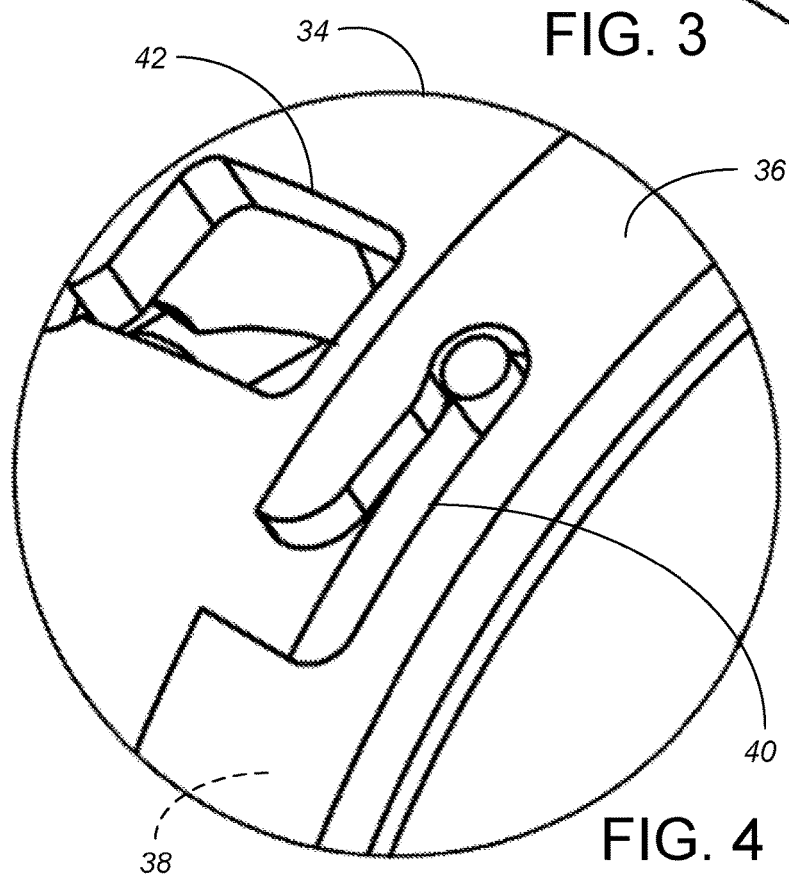
FIG. 4 is a close-up of one of the twist lock features of the stencil mask of FIG. 3, taken from line 4-4 in FIG. 3.
Figure 8:
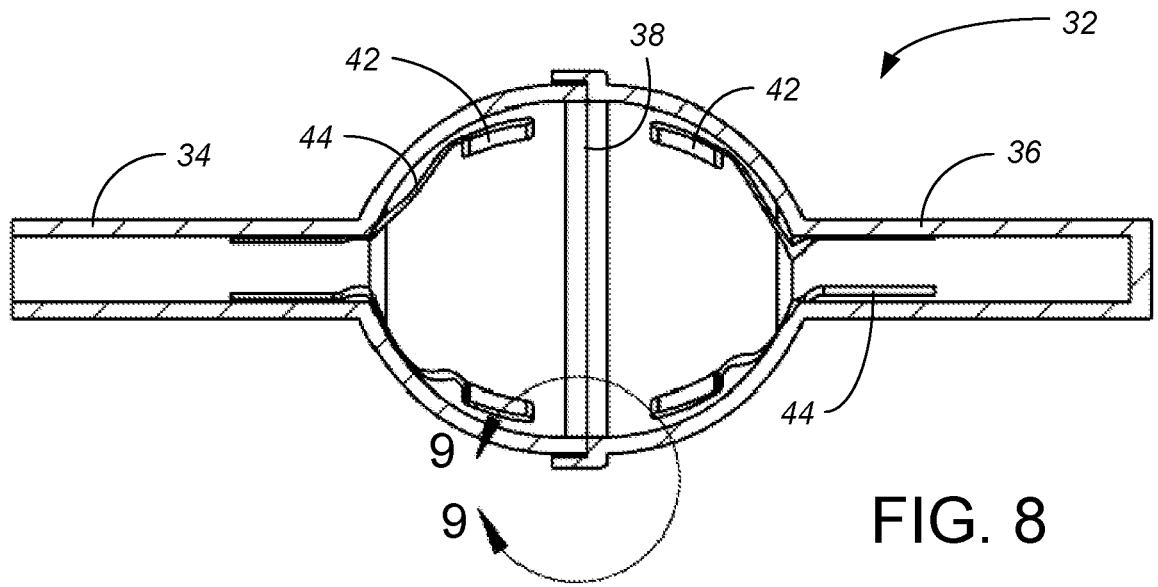
FIG. 8 is a cross-sectional view of the stencil mask of FIGS. 3-7, such as taken along cut lines 8-8 from FIG. 7.
Figure 9:
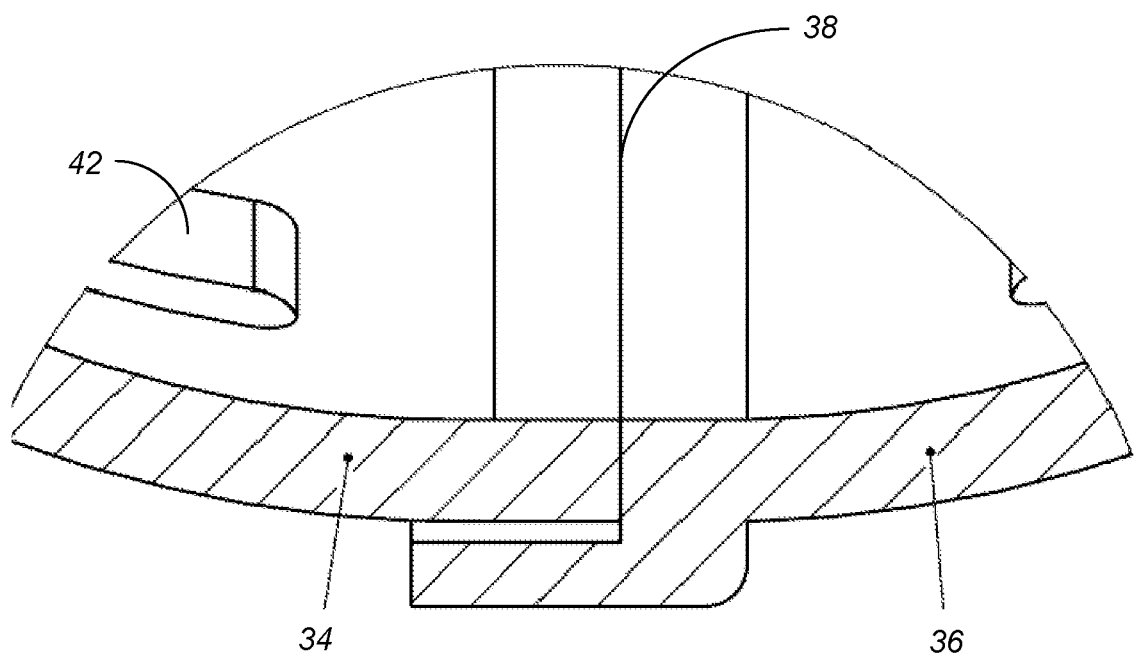
FIG. 9 is a close up of the parting line of the stencil mask of FIGS. 3-8, taken from line 9-9 in FIG. 8.

To join the two mask portions 34, 36 around the balloon 20B, the mask 32 part could include a twist lock feature 40 such as shown in FIG. 4, or alternatively a threaded feature (not shown) or a snap lock feature (not shown). The choice of how to secure the two mask portions 34, 36 together is driven by the relative complexity of either or both mask portions 34, 36 when formed out of the rigid mask material and by the selected mask manufacturing method. The preferred stencil mask 32 portions include a twist lock section 40 so it can be rapidly assembled around the balloon 20B. Another preferred embodiment includes a single screw thread (not shown) around the equator of the balloon 20, and a different embodiment includes three longitudinally directed screws (not shown) to attach the two hemispheres together. Workers skilled in the art will understand that there are many other alternative and equivalent ways to join two or more mask portions together around the balloon 20, 20A, 20B.

The walls of the mask 32 are relatively thin but still considerably thicker than the balloon wall thickness, such that the mask 32 is substantially rigid during the PVD process. For instance, the preferred mask 32 shown in FIGS. 3-9 has a wall thickness of 1.2 mm, formed by 3D printing. 3D printing is a good solution for creating parts in complex geometries, with inherent cost advantages when 3-D printing in small quantities over conventional subtractive machining processes. Current 3D printing methods preclude the use of micro-miniature features smaller than 0.5 mm, but are beneficial for quick formation of custom stencil masks for different balloon shapes. Alternative stencil mask production methods include injection molding and photolithography of complex geometries, photo chemical etching of flat thin metal that is then formed into cylindrical, cubical or conical shapes, electroforming of complex geometries, and machining and laser cutting/fabricating from tubular stock material. The stencil mask 32 is preferably semi-disposable, and long term durability/reusability is not a requirement at this time.

The mask walls have one or more cut-outs 42, 44 of the shape(s) desired of the metal pattern on the balloon surface. In the embodiment of FIGS. 3-9, the stencil mask 32 includes six rectangular electrode cut-outs 42 spaced around the periphery of the balloon 20B, such as for rectangular electrodes which are about 3 mm×5 mm. The preferred rectangular shapes 42 have soft radiused corners.

Figure 17:
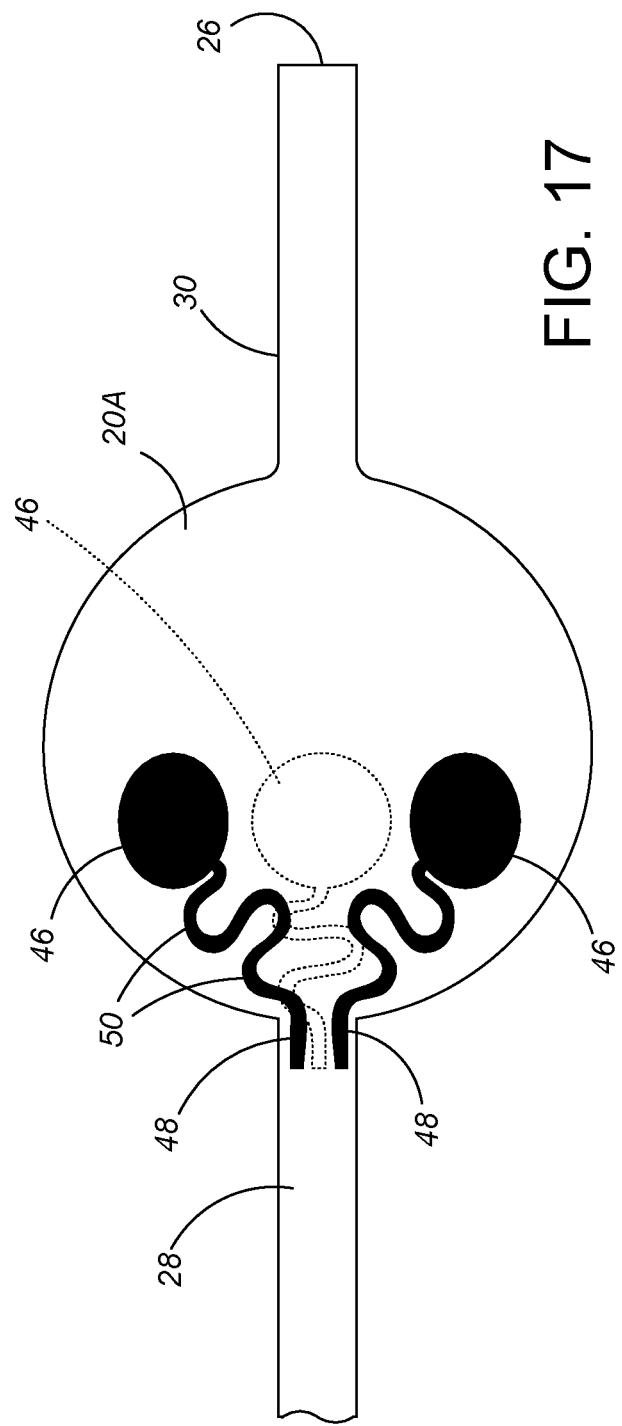
FIG. 17 is a side view of the balloon of FIG. 2, after application of the metal pattern using the PVD vacuum chamber of either FIG. 15 or FIG. 16.

Each electrode cut-out 42 has a thin lead cut-out 44 to create a lead which extends from the electrode (the actual electrodes 46 and leads 48 formed using the cut-outs 42, 44 are shown only in the final product of FIG. 17) to one of the proximal and distal tubing 28, 30. For instance, each lead cut-out 44 shown in FIGS. 3-9 has a uniform width of about 0.5 mm.

Each lead cut-out 44 is not straight, but rather includes one or more curves or undulations 50, such that the leads 48 appear "wavy" or "squiggly". The curves or undulations 50 are particularly important so the leads 48 will elastically yield and not break upon inflation of the balloon 20. During use, as the balloon 20 is pressurized and expands, a straight lead would experience tensile stress and could crack which would break electrical continuity. An undulating shape simply changes radius during balloon expansion, thereby spreading the tensile forces out and reducing the chances of a point failure. As shown, the lead cut-outs 44 should extend linearly for about 10 mm on the proximal or distal portion 28, 30. This length is primarily used for further electrical connection in the final assembly of the catheter device.

FIGS. 10-14 show an alternative stencil mask 32A for a cylindrical shaped balloon 20. This stencil mask 32A defines three electrode pads which are both longitudinally and cylindrically spaced on the outer diameter of the balloon 20. Lead cut-outs 44 define leads which extend from the electrode pads to the proximal tubing 28 of the balloon 20. The shortest of the lead cut-outs 44A, which does not extend substantially over the outer surface of the balloon 20, can be left straight, but the other two lead cut-outs 44B, 44C include one or more undulations 50. In the preferred embodiment shown in FIGS. 10-14, the proximal tubing portion 47 has an inner diameter of about 2.75 mm and the balloon portion 49 has an inner diameter of about 5.2 mm, both with a wall thickness of 1 mm. Each electrode pad cut-out 42 is 3×5 mm with rounded corners. The longest lead 44C includes six undulations 50 and extends longitudinally for about 34 mm over the outer cylindrical diameter of the balloon 20, and the mid-length lead 44B includes three undulations 50 and extends for about 17 mm over the outer cylindrical diameter of the balloon 20. Each lead cut-out 44A, 44B, 44C continues to extend linearly over the proximal conical taper portion 51 and further for about 4 mm on the proximal tubing 28.

In contrast to the stencil mask 32 shown in FIGS. 3-9, the alternative stencil mask 32A of FIGS. 10-14 is formed as a single piece, which can be slid over the proximal end 28 of the correspondingly shaped balloon 20. So that the stencil mask 32A will shield the distal tubing 30 area during PVD, an extension portion 52, having an inner diameter large enough for the balloon 20 to slide through, extends long enough to shield the distal tubing 30 area, before the open distal end 54 of the stencil mask 32A through which the balloon 20 can be inserted. An alternative stencil mask embodiment would include a narrower distal end with an inner diameter shaped similarly to the narrower proximal end 47 shown in FIGS. 10-14, requiring the compliant balloon to be fully deflated and compressed for insertion into the stencil mask.

FIGS. 15 and 16 show an alternative stencil mask 32B only in cross-section, to transform the balloon 20A shown in FIG. 2 into a balloon 20A having a patterned metal layer shown in FIG. 17. In this case, the patterned metal layer provides three electrodes 46 which are circular with a diameter of about 6 mm inches on only one of the balloon hemispheres, uniformly distributed at 120° intervals. Each lead 48 has three undulations 50, such as having an undulation radius of curvature of about 1-3 mm. After the electrodes 46 and leads 48 have been deposited on the balloon 20A without deforming or damaging the balloon 20A, either or both of the proximal and distal tubing sections 28, 30 may be trimmed to a desired length, including up to the end of each of the leads 48, as part of assembly into the final catheter device.

As will be understood, the specific dimensions of the stencil mask 32 and the specific dimensions of any cut-out 42, 44 can be tailored for the specific shape of the balloon and the specific functionality of the metal on the outer surface of the balloon. However, the stencil mask 32 and its cut-out(s) 42, 44 have several features which play an important role in dissipating heat from the balloon material during the PVD process. For instance, FIGS. 15 and 16 show examples of the PVD process, transforming the balloon 20A shown in FIG. 2 by adding the patterned metal layer to form the electrodes 46 and leads 48 shown in FIG. 17.

During the PVD process, a significant area of the balloon 20 will be in intimate contact with the inner diameter of the stencil mask 32, and the stencil mask 32 itself serves as a heat sink pulling heat away from the cut-out locations 42, 44 where metal is being deposited on the balloon 20. To have the stencil mask 32 better serve as a heat sink itself, the design should seek to maximize three properties of the stencil mask 32. First, the wall thickness of the stencil mask 32 should be thick—at least double and more preferably on the order of 10× or more—relative to the wall thickness of the balloon 20. In these embodiments, the stencil mask wall thicknesses of 1 mm and 1.2 mm significantly exceed the balloon wall thicknesses (such as in the range of 20-100 microns). While a thicker stencil mask wall thickness provides more heat sink, the stencil mask 32 still needs to be thin enough for vapor deposition of the metal layer through the cut-outs 42, 44. Second, to the extent possible, the material of the stencil mask 32 should be selected with an eye to higher specific heat capacities. Third, the area of the stencil mask 32 in contact with the balloon 20 should be large relative to the area of the cut-outs 42, 44. For instance, the cut-outs 42, 44 should make up less than ⅔ of the surface area of the balloon 20, and more preferably less than ⅓ of the surface area of the balloon 20, and most preferably less than ⅕ of the surface area of the balloon 20. Using the embodiment shown in FIGS. 3-9, the six 3×5 mm electrodes and their leads cover only about 5% of the balloon surface area. In the embodiment shown in FIGS. 10-14, where the balloon 20 has much less surface area, the three electrodes and their leads cover only about 12% of the balloon surface area. In the embodiment of FIGS. 15-17, the three electrodes 46 and their leads 48 cover only about 3% of the balloon surface area.

In addition to providing a heat sink in and of itself, the stencil mask 32 also provides a heat conduction path to pull heat away from the balloon 20 and transmit the heat preferably toward other heat sinks, possibly including to heat sinks outside the vacuum chamber. To increase heat conduction, the entirety of the stencil mask 32 (when assembled, if the stencil mask 32 requires assembly around the balloon 20) should be longitudinally continuous to at least one end, and more preferably to the proximal end. This means that the stencil mask 32 can define at most one metallic ring (not shown) on the balloon 20, but more preferably the entire metal pattern laid down on the balloon surface includes no circumferential rings. In the embodiments shown, for instance, each location on the stencil mask 32 includes a conduction path to the proximal end, where (as will be further described below) the stencil mask 32 can be received into the heat sink of a collet 56 (shown in FIGS. 16 and 18), and then can be further conducted away from the balloon 20.

To conduct heat longitudinally away from the balloon 20, the stencil mask 32 should be made from a material with a high coefficient of heat conduction. Primarily for this reason, the preferred stencil masks 32 are formed from metal, rather than from ceramic (which could achieve high specific heat and rigidity) or from polymer (which could reduce manufacturing costs). Preferred materials for the stencil mask 32 include copper, bronze, brass, steel including stainless steel, nickel, tin, silver, gold and tungsten and alloys thereof, most preferably aluminum. Even if 3D printed, the 3D printed substrate is preferably a metallic material, such as nickel or stainless steel. The thermal conductivity of a nickel or stainless steel 3D printed stencil mask 32 can be increased by coating the 3D printing with a more thermally conductive layer, such as by electro or electroless deposition, or even by standard PVD deposition on the 3D printed stencil mask 32. Preferred materials for the more thermally conductive layer on the stencil mask 32 are silver and copper.

Further heat control aspects of the present invention involve the construction of the vacuum chamber 58 and fixturing therein, further explained with reference to FIGS. 15, 16 and 18. A first step is to assemble the balloon 20 within its stencil mask 32 (or to assemble the stencil mask 32 around the balloon 20).

The PVD process takes place within a vacuum chamber 58, including one or more sputtering guns 60 extending through a wall of the vacuum chamber 58. The top 62 (or one of the walls, or a door) is preferably removable or attached such as with a hinge (not shown) to allow access for placement of the balloon 20 within its stencil mask 32 to be placed within the vacuum chamber 58.

As one optional preliminary step prior to placement into the vacuum chamber 58, the balloon surface may be pretreated by pre cleaning with isopropyl alcohol or other chemicals intended to clean the polymer surface without degrading the polymer, or by chemical etching, plasma arc, plasma cleaning, plasma etching, ion bombardment, ozone exposure or other surface modification process. If desired, the pretreatment may be carried out in the chamber 58, possibly under vacuum and possibly within a plasma, prior to energizing the magnetron tunnel and/or with suitable moveable shielding in front of the sputtering target. A primary purpose of the balloon surface pretreatment is to create free radicals in the polymer chain for bonding sites and thereby contribute to metal layer adhesion.

As another optional preliminary step prior to placement into the vacuum chamber 58, the balloon 20 and/or its stencil mask 32 may be cooled below ambient temperature prior to placement and fixturing in the vacuum chamber 58. For instance, the balloon 20 within its stencil mask 32 may be cooled in a standard refrigerator (to approx. 40° F.) or standard freezer (to approx. 20° F.)(neither shown) prior to placement and fixturing in the vacuum chamber 58.

A next step is to ensure that the balloon 20 is tight against the stencil mask 32 while the vapor deposition takes place. In the embodiment as depicted in FIG. 15, this is achieved by mounting the stencil/balloon combination on a shaft mandrel 64, such that the shaft mandrel 64 extends through the balloon 20. The preferred shaft mandrel 64 is longer than the balloon 20 such that it extends within the proximal and distal tubing portions 28, 30. When using the embodiment of FIG. 15, the mandrel 64 is sized so the proximal and distal tubing portions 28, 30 are a tight slip fit over the mandrel 64, creating a pressure tight seal between the proximal and distal tubing portions 28, 30 and the shaft mandrel 64. To support this pressure tight seal, the shaft mandrel 64 should be formed of a rigid material with a smooth, preferably cylindrical outer surface, with a preferred embodiment formed of stainless steel. The shaft mandrel 64 is hollow, and cylindrical stainless steel tubing is readily available in a variety of sizes to match whatever size is needed to mate with the inner diameter of the proximal and distal tubing portions 28, 30. The distal tip 66 of the shaft mandrel 64 is preferably capped or sealed closed, particularly if the distal tip 26 of the distal tubing 30 portion is not closed and/or if the distal tip of the stencil mask 32 is not closed. One or more holes 68 are cross drilled through the shaft 64 at a location within the balloon 20. During the PVD process, pressurized fluid is applied through the shaft mandrel 64 to the balloon interior, expanding the balloon 20 against the inner side of the mask wall. Once inflated (pressurized), the balloon 20 will conform tightly to the inside wall of the mask 32. The shaft mandrel 64 is preferably removable from the chamber 58, so the optional preliminary steps of pretreatment of the balloon surface and/or refrigerating/freezing can be performed on either the balloon 20 by itself, on the balloon 20 within the stencil mask 32 without the shaft mandrel 64, on the balloon 20 mounted on the shaft mandrel 64 without the stencil mask 32, or on the complete shaft mandrel/balloon/stencil mask assembly.

FIG. 15 shows one preferred vacuum chamber 58 layout for performing the PVD process. In some respects, the vacuum chamber 58 includes features typical of PVD vacuum chambers. One or more sputtering guns 60 are mounted, such as through the side walls of the chamber 58, pointed at the location of the metal deposition through the stencil mask 32 and onto the balloon 20. The sputtering guns 60 include the target providing the metal atoms which will be deposited on the balloon surface. If desired and appropriate for the size of the chamber 58, the sputtering guns 60 can alternatively be mounted entirely within the vacuum chamber 58. Each sputtering gun 60 may have its own cooling source or cooling mechanism CM. A vacuum pump 70 is provided to evacuate the chamber 58. As known in the PVD art, the vacuum pump 70 could be a diffusion pump, a cryogenic pump, a turbo molecular pump, a positive displacement vane single or dual stage pump or any other pump capable of producing high or ultrahigh vacuum conditions. An inert ionization gas source 72 allows the chamber 58 to be backfilled with the process gas which is ionized to create the plasma. A plasma power supply (magnetron cathode) 74 extends into the chamber 58 through a sealed electrical pass through, and the chamber 58 walls act as the magnetron anode. These various active components are all typically powered by electricity e.

In some respects, these various components can all be laid out as convenient to carry out the vapor deposition process. However, the sputtering guns 60 should be mounted such that the "mean free path distance", which is the distance from target to substrate, is optimal for the process gas pressure being used in the deposition process. The relationship between ideal mean free path distance and chamber pressure is represented by:

$$\text{Mean Free Path Distance (millimeters)} = 0.0495 / \text{chamber pressure (torr)}$$

In the preferred embodiments shown in FIGS. 15 and 16, the sputtering guns 60 are positioned about 50 mm away from the balloon/stencil mask assembly.

In the chamber layout shown in FIG. 15, the shaft mandrel 64 extends through the chamber lid 62, and a pressure source PS outside the chamber 58 can be controlled to pressurize the balloon 20 against the stencil mask interior. Because the shaft mandrel 64 makes intimate contact with the interior surface of the proximal and distal tubing portions 28, 30, the shaft mandrel 64 provides a heat conduction path to remove heat from the balloon 20 generated during the vapor deposition to a location outside the chamber 58. If desired, a separate heat sink or cooling mechanism CM (shown schematically) can assist in cooling the shaft mandrel 64, drawing heat away from the critical balloon surface.

The shaft mandrel 64 is rotationally driven by a motor M, turned on to slowly rotate the balloon/mask assembly during the deposition process, similar to barbecuing meat on a spit. The rotational speed used depends upon the speed of the PVD process (which depends both on the thickness of the metal layer needed and on the PVD parameters discussed below), but should be selected for smooth deposition of the metal layer. For instance, in one embodiment wherein the PVD process is run for 10-20 minutes, the rotational speed is in the range of 5 to 10 rpms, i.e., each surface being coated makes 50-200 passes in front of each sputtering gun 60. Preferably the motor M allows control over the rotational speed, possibly including reversing the motor direction, to achieve the most consistent metal layer deposition.

In the embodiment shown in FIG. 15, the motor M is mounted outside the chamber 58, such as on top of the chamber lid 62. This means that the rotating shaft mandrel 64 extends through the chamber lid 62, requiring sealing against the atmospheric pressure differential between the inside and outside of the vacuum chamber 58. As one option, the connection between the rotating shaft mandrel 64 and the chamber lid 62 can be a rotating union solid shaft pass-through (not separately shown) such as commercially available from Kurt J. Lesker Co. under part series no. KLFDxxx. The rotating union pass-through has a pass-through diameter equal to the outside diameter of the shaft mandrel 64.

The embodiment shown in FIG. 16 makes several changes relative to the embodiment shown in FIG. 15. In the embodiment of FIG. 15, the fixturing of the balloon/stencil mask assembly relies on the frictional contact between the inside diameter of the tubing 28, 30 and the outside diameter of the shaft mandrel 64. FIG. 16 uses a different fixturing set up, which relies on clamping a chucking device such as a collet 56 against the outside surface of the proximal end of the stencil mask 32. The collet 56 includes a lock nut or draw nut 76 that can be hand or tool rotated to tighten onto the outer surface of the stencil mask 32. The collet attachment allows quicker fixturing assembly and disassembly of the balloon/stencil mask assembly into and out of the vacuum chamber 58. The collet 56 preferably contacts the stencil mask 32 at a location on the stencil mask 32 proximal to all of the cut-outs 42, 44, so the tightening/clamping force of the lock nut 76 does not compress any of the cut-outs 42, 44 and instead can be bourn as a hoop stress on the continuous cylindrical outer surface of the proximal end of the stencil mask 32. In addition to serving as fixturing structure for the balloon/mask assembly, the collet 56 also acts as a heat sink within the chamber 58 for pulling heat away from the stencil mask 32 and thereby away from the balloon 20. For example, the collet 56 can be a size ER8 or ER20 collet with holder commercially available from www.toollots.com or www.exacttooling.com.

In the embodiment of FIG. 16, rotational motion is provided by a rotatable pipe section 78, driven by a motor M mounted inside the chamber 58, such as on the bottom of the chamber lid 62. By mounting the motor M within the chamber 58, there is no necessity to seal a rotating connection which extends through the chamber wall.

The embodiment of FIG. 16 also uses a different mechanism to remove heat from the inside surface of the balloon 20. Namely, while the embodiment of FIG. 15 uses a separately supplied fluid to pressurize the balloon 20 against the inside surface of the stencil mask 32, the embodiment of FIG. 16 not only supplies fluid pressure but also provides fluid flow inside the balloon 20. The embodiment of FIG. 16 includes an inlet flow pipe 80, preferably smaller than the inner diameter of the proximal tubing 28 portion, which does not make contact with the polymer material of the balloon 20 during the PVD process. Instead, as shown by arrows 82, cooling fluid is circulated down the inlet flow pipe 80, against the inside surface of the balloon 20 to quickly remove heat from the balloon material and regulate the temperature of the balloon material during the PVD process, up through the rotatable pipe section 78, and then out of the chamber 58 through an outlet flow port 84. The pressure, flowrate and temperature of the supply fluid can then be controlled from outside the chamber 58 during the PVD process. In one preferred embodiment, the cooling fluid is argon gas supplied at 15 psi and exhausting at atmospheric pressure. By using argon gas, any minor leakage of the cooling gas from inside the balloon 20 to out within the very low pressure in the chamber 58 does not significantly affect the PVD plasma. Alternatively, the cooling gas could be a different medically clean fluid, such as nitrogen or carbon dioxide. The cooling gas could also be a compressed gas which drops temperature upon expansion. In all cases, the cooling fluid must be clean to the applicable medical device regulatory standards for the device.

FIG. 18 depicts another embodiment of a fixturing arrangement, employing many of the concepts of FIG. 16. In this case, a carousel 86 is constructed which holds up to twelve balloons/stencil masks (only half shown in the cross-sectional view of FIG. 18) for simultaneous vapor deposition of patterned metal layers thereon in a single PVD batch process. For rotation, the entire carousel 86 is driven by a motor M, such as via a toothed belt drive 88. The pipe 78 for each balloons/stencil mask can then be counter-rotated by a separate motor M mounted on the bottom of the carousel 86 and driving each of the twelve pipes 78 via a toothed belt drive 90.

The carousel 86 of FIG. 18 is primarily constructed of three circular discs 92, 94, 96. Spaces between the discs 92, 94, 96 create the inward and outward flow path of the cooling fluid, so all twelve balloons/stencil masks can be simultaneously cooled with fluid flow from a single inlet supply outside the chamber 58. For instance, the hardware for the inlet 98 and the outlet 84 can be a coaxial dual flow rotary union such as commercially available from Rotary Systems, Inc. under part series no. RU009.

The balloon/mask assembly, pressurized so that the balloon 20 expands tightly to the inside of the mask 32, is located and slowly rotated in the vacuum chamber 58 for PVD deposition, which is performed using deposition parameters which avoid thermal deformation or degradation to the balloon 20. Evaporation of metal in the PVD process will invariably cause a temperature increase in the gas-state metal, as compared to the solid-state target. The substrate must have the capability to withstand the absorption of the thermal energy accompanying the deposition without thermal degradation or deformation of the polymer balloon base substrate. Alternately, a method must be employed to remove the thermal energy from the substrate before such degradation can occur. Under usual conditions, the temperature increase is sufficiently high as to cause dimensional distortion (shrinkage and deformation) of the thin walled balloons 20 when contact is made by the heated gas-state metal atoms. In addition to the various heat control methodologies discussed above, the creation of thin metal film on the thin-walled polymer balloons without deformation then depends closely on the conditions of the plasma formation and control.

Successfully producing thin metal films on a thin-walled polymer balloon 20 requires the balancing of competing parameters: Input of enough electrical energy to produce plasma that is sufficient to produce an adequate flux of target material in order to produce a deposition layer, but not so great an energy input that thermally damage to the substrate (i.e. the thin wall polymer balloons 20) occurs. The operation of the vacuum chamber 58 at higher pressure makes it easier to ionize the carrier gas into plasma, but also reduces the mean free path of all species in the gas/plasma thus requiring the target to be closer to the substrate, but that increases the thermal load (heating) of the substrate (polymer balloons 20). Conversely, operation of the chamber 58 at lower than ideal pressure increases the mean free path, but requires greater (voltage) energy input to ionize the lesser amount of inert gas. This greater energy input causes excess heating of the target, which in turn is carried by the vapor cloud to the more distant substrate, again increasing the risk of thermal damage. Judicious balancing of these parameters produces successful deposition of metal film patterns on thin polymer balloons 20.

In the preferred PVD setup shown in FIG. 15, the sputtering guns 60 use somewhat older technology power supplies which operate at RF frequencies that are not currently popular. The sputtering guns 60 using "archaic" power supplies generate less energy, which is beneficial toward minimizing or eliminating thermal degradation of the balloon substrate. The energy input to evaporate metal must be sufficiently low so as to prevent overheating and deformation/degradation of the polymer surface at the metal/polymer bonding site contact. The wattage must be low enough not to melt or thermally damage the polymer balloon 20. The frequency is selected to provide an efficient rate of deposition at the low power. The pressure is selected to optimize deposition. Too high a pressure slows down the deposition process and can result in part damage, but too low a pressure also slows down the deposition process.

Deposition using DC power sources with power typically no greater than 200 watts (per balloon/mask assembly) has been successful in producing metallic films without distorting the balloons 20. The maximum power can be adjusted for the composition of the layer. Difficult to deposit materials such as titanium may be run at higher power; it is the deposition rate which must be kept below a critical value in order to not distort the balloon 20. Materials which deposit more easily (i.e. faster) must be run at a lower power level. The most preferred setting for deposing gold onto a PET balloon 20 operates at about 20 watts per balloon/mask assembly.

Deposition using AC power sources (RF magnetron power supplies at 13.56 Mz and plasma supplies in the low to moderate RF range of few kilohertz to 100 KHz) have also been used to deposit metallic films without distorting the balloons 20. The power must be kept below a critical value which depends on both the polymer balloon material, the metal being deposited, and the frequency of the power source.

The ideal power settings for plasma generation are based on the amount of the target surface that is intended to be evaporated. The actual total surface area is not important, except that a larger surface area will provide longer intervals of surface before depletion. The critical power measure is the energy (watts) per amount of surface area that is being utilized, which is preferably less than about 200 watts/square inch of effective target surface area. The optimal value for plasma power is 50 watts/square inch of effective target surface area. The power settings for the magnetron focusing ring are less crucial as they do not impart significant heat to the balloon substrate.

The preferred PVD uses a pressure from less than 1 micron (0.001 torr or 1 milli-torr), to 500 microns (or more), and more preferably in the range of 0.8 to 1.2 milli-torr. The PVD uses DC power or AC power from a less than 1 kilohertz to 200 KHz and possibly as high as 13.56 MHz, and more preferably a moderate frequency AC power in the range of 4-10 KHz. The combination of parameters allows for metal deposition on thin walled balloons 20 while maintaining the integrity of the polymer and shape of the balloon 20. The preferred power, pressure and frequency depend on the metal being deposited and the physical properties of the polymer substrate and dimensions and shape of the object being deposited upon. The objective is to provide enough energy to deposit the metal but not so much as to thermally degrade, dimensionally alter or otherwise compromise the thin walled balloon 20. One example of successful conditions is an applied DC plasma excitation power of 20 W to one or more targets whose total effective surface area is 0.418 square inches, and using a magnetron sputtering source/e.g. MEIVAC-brand MAC Sputter Deposition Source, with all target(s) spaced 5 cm from the substrate operating, and at an argon pressure of 0.8 milli-torr to 1.2 milli-torr.

A refinement of this invention is the introduction of ionized gas at higher pressure into a smaller volume "pocket" (not shown) which is open to, and situated along the side, of the main volume of the vacuum chamber 58. This refinement maintains the introduced process gas (argon) at a higher pressure pending expansion into the main volume. By temporarily maintaining a higher pressure, the ionization voltage can be reduced thus further lowering the risk of thermal damage to the balloon substrate. This refinement either improves the sputtering deposition rate without increasing the applied power, or provides the same deposition rate at reduced power thus further reducing the thermal effects to the least heat tolerant polymer substrates.

The preferred process maintains a generally uniform distribution of ion plasma within the volume of the chamber 58, and is thus distinct from ion beam assisted deposition (IBAD) where a focused ion beam is aimed directly at the substrate while the deposition is taking place. The preferred refinement process, which might be called ion plasma augmented deposition (IPAD), involves the flooding of the vacuum chamber 58 with ionized gas, typically argon. Regardless of the choice of specific process gas, a stream of process gas is directed into the vacuum chamber 58 through or past an electrode which is energized to ionize the gas as it passes into the chamber 58.

The gas at the electrode can be at a higher pressure than that maintained within the vacuum chamber 58, which allow the refinement process to achieve ionization at a lower voltage. The expansion of the gas into the volume of the vacuum chamber 58 allows for the pressure to develop to the value used for deposition. This process vacuum is maintained at a steady state by a balanced rate of expanding plasma gas admitted versus the pumping speed of the vacuum pump 70.

In one preferred embodiment, an initial PVD process deposits a titanium layer on the masked polymer balloon 20 prior to deposition of the active (typically gold) layer. The titanium base layer makes a strong attachment to the widest variety of polymers. The preferred PVD setup shown in FIG. 15 deposits both layers in a single vacuum operation by using two sputtering guns 60, one gun 60 per metal type.

However, a gold layer directly on top of the titanium layer is problematic because the electronegative potentials of Ti and Au are so far apart that a strong galvanic coupling will occur. Further, the human body is internally saline wet, so the electrolyte naturally exists to support the galvanic coupling of the Ti and Au. One preferred embodiment uses an intermediate layer between the Ti and Au layers, using a third metal which splits the electronegative difference, i.e., whose potential is about midway between Ti and Au. The most preferred third metals, for the intermediate layer between Ti and Au, are palladium or silver. The intermediate metal layer mitigates in-situ corrosion. If a three-layer stack is used, all three layers can be deposited in a single vacuum operation by using three sputtering guns, one gun per metal type.

Other embodiments substitute alloys containing Ti, Pd or Ag, or Au for the pure metal in any or all of the three metal layer constructions. Other embodiments can also use other metals with high conductivity and inertness. For instance, Pt can be used in medical electrodes, including in alloyed Pt/Ir electrodes and radiographic markers. Cu and Sn are both highly electrically and thermally conductive at relative low cost, such as for use in some MRI compatible applications. Multi-layer constructions such as the preferred embodiments maximize mechanical adhesion, stretch ability, plasticity and elasticity, robustness against delamination, solderability or joinability of leads and other components, sanitization compatibility, anti-microbial properties, mechanical wear robustness, sheer strength, tensile strength, IR reflectivity (sensors or laser delivered and guided energy for ablation and stimulation), skin depth impedance, thermal & electrical insulation or conduction, reduced gas permeability, sonic/acoustic energy reflection or delivery, robustness against fracturing, flaking or abrasion, electrical performance, biocompatibility, corrosion resistance, mechanical/dimensional conformability and flexibility under expansion or compression. The preferred multi-layer constructions also maximize folding tolerance, solder ability, thermal performance, and radiopacity (density).

The preferred PVD setup shown in FIG. 16 uses two sputtering guns 60, but both can use the same target metal. In this embodiment, the sputtering guns 60 are angled relative to the longitudinal and rotational axis of the balloon/ stencil mask assembly. Angling of the sputtering guns 60 is preferred when the features being deposited on the balloon 20 are not on the equator of the spherical balloon 20, i.e., so the angle of the gun 60 is as much as possible perpendicular to the deposition surface of the balloon substrate. Further, for at least some metals such as gold, if the proper process is used, excellent adhesion can be achieved without a titanium base layer. Excellent gold adhesion to the polymer substrate is achievable with the use of a plasma arc, in-chamber 58, prior to energizing the sputtering guns 60. In effect, we are breaking polymer bonds with the plasma field and the gold atoms then shortly thereafter occupy those bonds.

The deposited metal ends up coating the entire outside of the mask 32, plus the outer surface of the balloon 20 where the mask 32 has been cut-out in patterns. While carefully managing heat to avoid balloon degradation, the deposited metal layers may vary from essentially an atomic monolayer to enhance adhesion to many tens of microinches of metal to provide the final functionality desired. Functional layers created by the preferred PVD method s can be as thin as 1000 to 5000 angstroms (0.000004" to 0.000020"). The thin metal deposits avoid design challenges where space constraints are significant, such as in smaller diameter vasculature. On the other end of the spectrum, thicknesses of up to about 4 μm (160 microinches) are achievable with just the PVD of the present invention. Even thicker metal coatings, such as well over 25 μm (1,000 microinches), can be achieved with the addition of electroplating after a PVD seed layer is applied.

Additionally there may be one or more intermediary layers, between the balloon polymer and the upper functional metal layer to provide desired properties of mechanical adhesion, robustness and corrosion resistance.

The metallic coating created by the preferred process is thin, creating a low device profile. The metallic coating is both adherent to the polymer, and flexible such that it will not fracture or delaminate under nearly any force vector which would be experienced in the medical device application. The patterned metallic coating has robustness in the form of flexibility, folding, anti-fracturing, anti flaking, abrasion, anti-corrosion, and dimensional conformity. The resultant balloons 20 are fully biocompatible. The present invention also results in material consumption and process reductions as compared to the prior art.

Plating and electroplating may be incorporated before or after the PVD process for certain applications, for instance component manufacturing applications that require a thicker metal deposit on the polymer for the purpose of increased radiopacity brightness. Or, to alter the grain structure of the additional metal deposited for purposes including but not limited to enhanced structural integrity, aesthetics, blood/ tissue interaction, and other potential performance enhancements. Plating and electroplating can also be used possibly for process time reductions due to plating/electroplating depositing metal faster than most vacuum deposition methods.

The balloons 20 of the present invention have a variety of uses in medical devices such as but not limited to ablation, cauterization, expansion, temperature measurement, pO2 measurement, blood chemistry measurement, blood pressure measure, sensing not limited to mapping and guiding as well as thermal sensors, electrical stimulation, various electrode designs on a single balloon 20 to accommodate the different anatomy from patient to patient or areas of the body for instance various thicknesses of an arterial wall. The patterned metal layer is used for electrical contacts and other purposes. For instance, the thin metal electrodes adhered onto the thin walled flexible polymer balloon 20 will conduct a current, resulting in heat or a signal used in the localized area, from RF energy or magnetic/electromagnetic/electrical energy fields as the source of the energy, for use in ablation or medical procedures requiring heat, with or without the use of lead paths/wires to the electrodes. The patterned metal layer can be used as lead or leadless electrodes implemented on the balloon 20 or flexible medical polymer, reactive to energy sources including but not limited to MRI, RF and other magnetic or electromagnetic fields for the conduction/induction of the metal which is applied to the polymer. Energy sources such as an MRI, C-Arm fluoroscopy and ultrasound can be used for image guidance of the procedure and sensing/signal transfer as well. Without the need for wire leads, the device's overall dimensional profile can be reduced, and the complexity of manufacturing and installing fine lead wires within the catheter construction is eliminated therefore reducing costs and risks of device failures.

Although the present invention has been described with reference to preferred embodiments, workers skilled in the art will recognize that changes may be made in form and detail without departing from the spirit and scope of the invention.

What is claimed is:

1. A balloon for a medical grade device to be deployed within a human body, comprising:
   flexible polymer tubing including a proximal tubing portion and a distal tubing portion each having a tubing outer diameter and a tubing wall thickness; a balloon disposed between the proximal tubing portion and the distal tubing portion, the
   balloon being formed continuously from the polymer tubing with the proximal and distal tubing portions, the balloon having a balloon outer diameter of no greater than 50 mm and which is at least 1.5 times the tubing outer diameter, the balloon having a balloon wall thickness which is thinner than the tubing wall thickness, so as to be stretchable radially outward when pressure is increased inside the balloon relative to outside the balloon, and
   a patterned metal layer on the balloon, the patterned metal layer being deposited on the balloon by physical vapor deposition through a stencil mask without deforming or degrading the polymer material of the balloon, the patterned metal layer covering less than two thirds of the balloon and having a metal layer thickness of no greater than about 4 µm, the patterned metal layer includes a plurality of layers comprising a bottom layer of titanium, a middle layer selected from palladium and silver, and an upper layer of gold.

2. The balloon of claim 1, wherein the patterned metal layer comprises an undulating lead.

3. The balloon of claim 2, wherein the patterned metal layer comprises a plurality of electrodes, each electrode having an undulating lead which extends to the proximal tubing portion.

4. The balloon of claim 2, wherein the patterned metal layer comprises no more than a single circumferential ring on the balloon.

5. The balloon of claim 1, wherein the polymer is selected from the group consisting of polyethylene terephthalate, urethane, polyurethane, polyimide, polyamide, Pebax, silicon, nylon, polyethylene, polyvinyl chloride, polyarylenesulfide, mixtures of ethylene-butylene-styrene block copolymer and low molecular weight polystyrene, mixtures of ethylene-butylene-styrene block copolymer, low molecular weight polystyrene and polypropylene; polyester copolymer; thermoplastic rubber; silicone-polycarbonate copolymer; ethylene-vinyl acetate copolymer; and crosslinked ethylene-vinyl acetate copolymer.

6. The balloon of claim 1, wherein the tubing outer diameter is less than about 10 mm and the tubing wall thickness is less than about 2 mm.

7. The balloon of claim 6, wherein the proximal tubing portion and the distal tubing portion are each at least 2 mm in length, and having a balloon wall thickness in the range of 0.02-0.04 mm.

8. The balloon of claim 1, wherein the balloon outer diameter will expand under a 10 atm pressure difference to within the range of 102-150% of its unpressurized diameter.

9. The balloon of claim 2, wherein the undulating lead extends linearly for at least about 4 mm on the proximal tubing portion or the distal tubing portion.

10. The balloon of claim 9, wherein the undulating lead has a uniform width of about 0.5 mm.

11. The balloon of claim 4, wherein the patterned metal layer comprises no circumferential rings on the balloon.

12. A balloon for a medical grade device to be deployed within a human body, comprising:
    flexible polymer tubing including a proximal tubing portion and a distal tubing portion each having a tubing outer diameter and a tubing wall thickness;
    a balloon disposed between the proximal tubing portion and the distal tubing portion, the balloon being formed continuously from the polymer tubing with the proximal and distal tubing portions, the balloon having a balloon outer diameter which is larger the tubing outer diameter, the balloon having a balloon wall thickness which is thinner than the tubing wall thickness, so as to be stretchable radially outward when pressure is increased inside the balloon relative to outside the balloon, and
    a patterned metal layer deposited directly on an outer surface of the balloon, the patterned metal layer covering less than two thirds of the balloon and having a metal layer thickness of no greater than about 4 µm, wherein the patterned metal layer comprises a plurality of electrodes, each electrode having an undulating lead which extends to the proximal tubing portion, the patterned metal layer includes a plurality of layers comprising a bottom layer of titanium, a middle layer selected from palladium and silver, and an upper layer of gold, and wherein the patterned metal layer comprises no circumferential rings on the balloon.

13. The balloon of claim 12, wherein the polymer is selected from the group consisting of polyethylene terephthalate, urethane, polyurethane, polyimide, polyamide, Pebax, silicon, nylon, polyethylene, polyvinyl chloride, polyarylenesulfide, mixtures of ethylene-butylene-styrene block copolymer and low molecular weight polystyrene, mixtures of ethylene-butylene-styrene block copolymer, low molecular weight polystyrene and polypropylene; polyester copolymer; thermoplastic rubber; silicone-polycarbonate copolymer; ethylene-vinyl acetate copolymer; and crosslinked ethylene-vinyl acetate copolymer.

14. The balloon of claim 12, wherein the balloon has a balloon outer diameter of no greater than 50 mm and which is at least 1.5 times the tubing outer diameter, and has a balloon wall thickness in the range of 0.02-0.04 mm, wherein the balloon outer diameter will expand under a 10 atm pressure difference to within the range of 102-150% of its unpressurized diameter, wherein the tubing outer diameter is less than about 10 mm and the tubing wall thickness is less than about 2 mm, wherein the proximal tubing portion and the distal tubing portion are each at least 2 mm in length, and wherein the undulating lead extends linearly for at least about 4 mm on the proximal tubing portion or the distal tubing portion.

15. A method of forming a balloon with a metal pattern thereon for a medical grade device to be deployed within a human body, the method comprising:

provising a balloon formed from flexible polymer tubing between a proximal tubing portion and a distal tubing portion, each of the proximal and distal tubing portions having a tubing outer diameter and a tubing wall thickness, the balloon having a balloon outer diameter which is larger than the tubing outer diameter, the balloon having a balloon wall thickness which is thinner than the tubing wall thickness, so as to be stretchable radially outward when pressure is increased inside the balloon relative to outside the balloon, the balloon having an external surface area;

inflating the balloon within a stencil mask, the stencil mask being rigid relative to the balloon, the inflation causing the balloon to increase in volume from a smaller volume to a constant interior volume of the stencil mask and such that a first portion of the balloon's external surface area is in intimate contact with an inside of the stencil mask and a second portion of the balloon's external surface area is exposed through one or more openings in the stencil mask; and depositing a patterned metal layer on the balloon by physical vapor deposition through the stencil mask while the balloon is inflated within the stencil mask, such that the patterned metal layer covers the second portion of the balloon's external surface area.

16. The method of claim 15, further comprising:

prior to depositing the patterned metal layer on the balloon, cooling the balloon within the stencil mask to below ambient temperature.

17. The method of claim 15, further comprising:

prior to depositing the patterned metal layer on the balloon, chemically cleaning a surface of the balloon to create free radicals for metal layer adhesion.

* * * * *